United States Patent [19]

Yagawara et al.

[11] Patent Number: 4,984,446
[45] Date of Patent: Jan. 15, 1991

[54] GAS DETECTING DEVICE AND GAS DETECTING SYSTEM USING THE SAME

[75] Inventors: Shinji Yagawara; Wasaburo Ohta, both of Yokohama; Junji Manaka, Kawasaki, all of Japan

[73] Assignees: Ricoh Company, Ltd.; Ricoh Seiki Company, Ltd., both of Tokyo, Japan

[21] Appl. No.: 356,067

[22] Filed: May 24, 1989

[30] Foreign Application Priority Data

May 27, 1988 [JP] Japan ................................. 63-131098

[51] Int. Cl.$^5$ ........................................... G01N 27/12
[52] U.S. Cl. ..................... 73/31.06; 338/34; 422/98
[58] Field of Search ................ 73/23, 27 R, 31.06; 422/83, 98; 338/34

[56] References Cited

U.S. PATENT DOCUMENTS

| 4,358,950 | 11/1982 | Chang | 73/23 |
| 4,377,944 | 3/1983 | Hishii et al. | 73/23 |
| 4,580,439 | 4/1986 | Manaka | 73/23 |

FOREIGN PATENT DOCUMENTS

| 0265834 | 5/1988 | European Pat. Off. | 73/23 |
| 0291462 | 11/1988 | European Pat. Off. | 73/23 |
| 191953 | 3/1986 | Japan | |
| 172948 | 7/1988 | Japan | 73/23 |

OTHER PUBLICATIONS

T. Oyabu, "Sensing Characteristics of SnO$_2$ Thin Film Gas Sensor", J. Appl. Phys., 53, 1982, pp. 2785–2787 (p. 65).
H. Ogawa et al., "Electrical Properties of Tin Oxide Ultrafine Particle Films" The Electrochemical Society, vol. 128, No. 9, pp. 2020–2025, 1981 (p. 66).

Primary Examiner—Hezron E. Williams
Assistant Examiner—Joseph W. Roskos
Attorney, Agent, or Firm—Oblon, Spivak, McClelland, Maier & Neustadt

[57] ABSTRACT

A gas detecting device includes a substrate, an insulating layer supported by the substrate, first and second pairs of detection leads formed on the insulating layer, a heater lead formed on the insulating layer, the first and second pairs of detection leads being heated by passing a heater driving current through the heater lead, a gas sensitive layer formed of a gas sensitive material and provided so as to partially make contact with the first and second pairs of detection leads, and a passivation layer formed so as to cover the first and second pairs of detection leads and the heater lead. A gas detection signal is output from the gas sensitive layer through one of the first and second pairs of detection leads. A gas detecting system including the above gas detecting device is also provided.

34 Claims, 9 Drawing Sheets

GAS DETECTING DEVICE AND GAS DETECTING SYSTEM USING THE SAME

BACKGROUND OF THE INVENTION

The present invention generally relates to a gas detecting device, and particularly to a gas detecting device which has four terminals and is suitable for a gas leak alarm designed to detect gas such as LP gas and commercialized gas. Further, the present invention relates to a gas detecting system which employs the 4-terminal gas detecting device.

Referring to FIG.1, there is illustrated a gas detecting system including a conventional gas detecting device 100. A pair of heater coils 112 is covered by a sintered ceramics member 115 of a size of 2 mm=2 mm to 3 mm=3 mm, which is formed of a metal oxide semiconductor. The sintered ceramics member or gas sensitive member 115 is sensitive to gas. The heater coils 112 are connected to four terminals 113, which penetrate a base 111. The four terminals 113 are connected to a variable power source 116, a constant power source 117 and a resistor R1. During a gas detecting operation, the gas sensitive member 115 is heated. When the gas sensitive member 115 reacts to gas, the resistance of the gas sensitive member 115 decreases due to gas absorption occurring on an exposed surface of the gas sensitive member 115. A variation in resistance of the gas sensitive member 115 is extracted as a variation in voltage across the register R1.

However, the contact resistance between the gas sensitive member 115 and the pair of the heater coils 112 depends on a condition of contact formed therebetween. The occurrence of variation in contact resistance prevents accurate gas detection.

An improved gas detecting device has been proposed in Japanese Laid-Open Patent Application No. 61-191953. The proposed gas detecting device includes a substrate, an insulator, a pair of detection leads, a passivation layer, and a gas sensitive layer. The pair of detection leads is arranged on the insulator so that an end of each of the detection leads is opposite to each other. The detection leads are partially covered by the gas sensitive layer at the opposed ends thereof. The rest of each of the detection leads is covered with the passivation layer.

However, even by the proposed structure for the gas detecting device, the gas detection signal varies depending on the contact resistance formed between the detection leads and the gas sensitive layer.

The inventors have proposed a further improved gas detecting device in U.S. patent application Ser. No. 07/288,279 filed on Dec. 22, 1988, the disclosure of which is hereby incorporated by reference. However, even by the proposed structure, it is difficult to completely remove the influence of variation in contact resistance.

SUMMARY OF THE INVENTION

It is therefore a general object of the present invention to provide an improved gas detecting device in which the above-mentioned disadvantages are eliminated.

A more specific object of the present invention is to provide a gas detecting device capable of generating a gas detection signal which is immune to a variation in contact resistance between a gas sensitive layer and detection leads through which the gas detection signal is output.

The above objects of the present invention can be achieved by a gas detecting device including a substrate, an insulating layer supported by the substrate, first and second pairs of detection leads formed on the insulating layer, a heater lead formed on the insulating layer, the first and second pairs of detection leads being heated by passing a heater driving current through the heater lead, a gas sensitive layer formed of a gas sensitive material and provided so as to partially make contact with the first and second pairs of detection leads, and a passivation layer so as to cover the first and second pairs of detection leads and the heater lead, a gas detection signal being output from the gas sensitive layer through one of the first and second pairs of detection leads.

The above-mentioned objects of the present invention can also be achieved by a gas detecting device including a substrate, an insulating layer supported by the substrate, first, second, third and fourth pairs of detection leads formed on the insulating layer, the detection leads of each of the first, second, third and fourth pairs extending in the opposite directions, a heater lead formed on the insulating layer and located between a first group consisting of the first and second pairs of detection leads and a second group consisting of the third and second detection leads, the first to fourth pairs of detection leads being heated by passing a heater driving current through the heater lead, a gas sensitive layer formed of a gas sensitive material and provided so as to partially make contact with the first groups of detection leads, a temperature sensitive layer formed of a temperature sensitive material and provided so as to partially make contact with the second group of detection leads, and a passivation layer so as to cover the first and second pairs of detection leads and the heater lead, and the temperature sensitive layer, a gas detection signal being output from the gas sensitive layer through one of the first and second pairs of detection leads.

The aforementioned objects of the present invention can also be achieved by a gas detecting device including a substrate, an insulating layer supported by the substrate, a pair of detection leads formed on the insulating layer, a pair of heater leads formed on the insulating layer, the pair of detection leads being heated by passing a heater driving current through each of the paired heater leads, a gas sensitive layer formed of a gas sensitive material and provided so as to partially make contact with the pair of detection leads and the pair of heater leads, and a passivation layer so as to cover the pair of detection leads and the pair of heater leads and cover around the gas sensitive layer, a gas detection signal being output from the gas sensitive layer through the pair of detection leads.

Another object of the present invention is to provide a gas detecting system which uses the gas detecting device improved by the present invention.

The above object of the present invention can be achieved by a gas detecting system including a substrate, an insulating layer supported by the substrate, first and second pairs of detection leads formed on the insulating layer, a heater lead formed on the insulating layer, heating the first and second pairs of detection leads, a passivation layer so as to cover the first and second pairs of detection leads and the heater lead, a gas sensitive layer formed of a gas sensitive material and provided so as to partially make contact with the first and second pairs of detection leads, first power source means, connected to the heater lead, for passing a heater driving current through the heater lead, second power source means, connected to the first pair of detection leads, for applying a predetermined voltage to the gas sensitive layer through the first pair of detection leads, and voltage monitoring means, connected to the second pair of detection leads, for monitoring a variation in voltage generated in the gas sensitive layer through the second pair of detection leads.

The above object of the present invention can also be achieved by a gas detecting system including a substrate, an insulating layer supported by the substrate, a pair of detection leads formed on the insulating layer, a pair of heater leads formed on the insulating layer, heating the pair of detection leads, a gas sensitive layer formed of a gas sensitive material and provided so as to partially make contact with the pair of detection leads and the pair of heater leads, a passivation layer so as to cover the pair of detection leads and the pair of heater leads and cover around the gas sensitive layer, first power source means, connected to one of the pair of heater leads, for passing a first heater driving current through the one of paired heater leads, second power source means, connected to the other one of paired heater leads, for passing a second heater driving current through the other one of paired heater leads, third power source means, connected to the pair of detection leads, for applying a predetermined voltage to the gas sensitive layer through the pair of detection leads, and voltage monitoring means, connected to the pair of heater leads, for monitoring a variation in voltage generated in the gas sensitive layer through the pair of detection leads.

The above-mentioned object of the present invention can also be achieved by a gas detecting system including a substrate, an insulating layer supported by the substrate, a pair of detection leads formed on the insulating layer, a pair of heater leads formed on the insulating layer, heating the pair of detection leads, a gas sensitive layer formed of a gas sensitive material and provided so as to make contact with the pair of detection leads and the pair of heater leads, a passivation layer so as to cover the pair of detection leads and the pair of heater leads and cover around the gas sensitive layer, power source means, connected between the heater leads, for periodically supplying the pair of heater leads with a heater driving current, switching means, connected to the pair of heater leads so as to form a driving current loop consisting of the pair of heater leads and the power source means, for alternately making and breaking the driving current loop, and voltage monitoring means, connected to the pair of gas sensitive layer, for monitoring a variation in voltage generated in the gas sensitive layer.

Other objects, features and advantages of the present invention will become apparent from the following detailed description when read in conjunction with the accompanying drawings.

DESCRIPTION OF THE PREFERRED EMBODIMENTS

Figure 1:
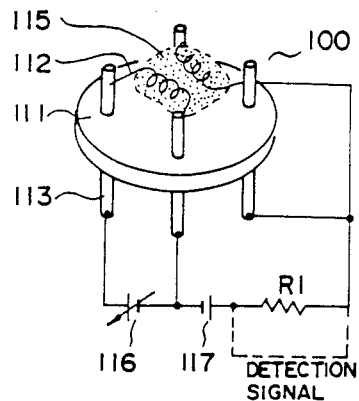
FIG.1 is a view illustrating a conventional gas detecting system.

A description is given of a first preferred embodiment of the present invention with reference to FIGS.2 through 5. A gas detecting device of the first embodiment includes a substrate 1 made of a heat-resistant material, such as a silicon substrate and a nickel plate. A groove 7 is formed in a center portion of the substrate 1. A bridge 6 made of an electrically insulating material such as silicon dioxide ($SiO_2$), alumina ($Al_2O_3$), silicon nitride ($Si_3N_4$), and tantalum oxide ($TaO_5$) is formed across the groove 7 and diagonally couples corner portions of the substrate 1. Two pairs of detection leads 3e, 3f, and 4e, 4f are formed on the bridge 6. An end of the detection lead 3e faces an opposed end of the detection lead 3f. Similarly, an end of the detection lead 4e faces an opposed end of the detection lead 4f. The detection leads 3e and 3f run parallel with the detection leads 4e and 4f. A heater lead 2c is formed on the bridge 6 in parallel with the two pairs of detection leads 3e, 3f, and 4e and 4f. The heater lead 2c is wider than the pairs of the detection leads 3e, 3f, 4e and 4f. The detection leads 3e, 3f, 4e and 4f, and the heater lead 2c are made of a conductive material such as gold (Au), platinum (Pt), palladium (Pd), irridium (Ir), rhodium (Rh), nickel chromium (NiCr), tantalum nitride (Ta$_2$N), silicon carbon (SiC), kanthal or the like.

A gas sensitive layer 5 is formed so as to make contact with end portions of the detection leads 3e, 3f, 4e and 4f, which are exposed through contact holes 3c, 3d, 4c and 4d formed in the passivation film 8. The gas sensitive layer 5 are formed of tin dioxide (SnO$_2$), ferrous oxide (Fe$_2$O$_3$) and zinc oxide (ZnO) by evaporation, sputtering, chemical copper deposition, ion plating, or the like.

The passivation film 8 covers the entire surface of the substrate 1 except for portions where the contact holes 3c, 3d, 4c and 4d (FIG.5) are to be formed, and portions at which bonding pads 2a, 2b, 3a, 3b, 4a and 4b are to be formed. The contact holes 3c and 3d are related to the detection leads 3e and 3f, respectively. The contact holes 4c and 4d are related to the detection leads 4e and 4f, respectively. The bonding pads 3a and 3b are formed at end portions of the detection leads 3e and 3f, respectively. Similarly, the bonding pads 4a and 4b are formed at end portions of the detection leads 4e and 4f, respectively. The bonding pads 2a and 2b are formed at end portions of the heater lead 2c. The passivation film 8 is formed of an electrically insulating material such as a silicon dioxide (SiO$_2$), alumina (Al$_2$O$_3$), silicon nitride (Si$_3$N$_4$), tantalum oxide (TaO$_5$), or the like.

Figure 2:
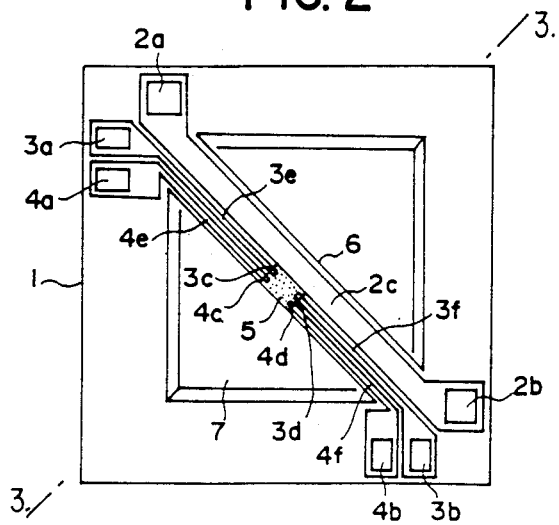
FIG.2 is a plan view of a first preferred embodiment of the present invention.
Figure 3:
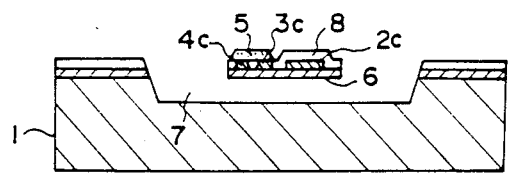
FIG.3 is a sectional view taken along line 3—3 shown in FIG.2.
Figure 4:
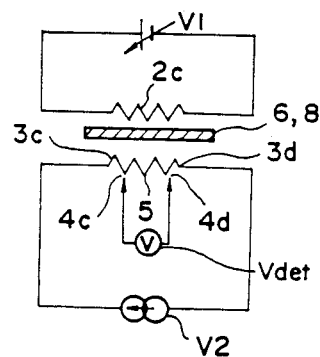
FIG.4 is a circuit diagram of a gas detecting system using the gas detecting device of FIGS.2 and 3.
Figure 5:
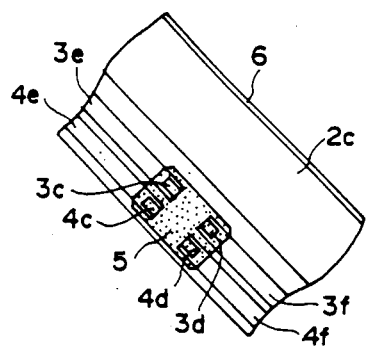
FIG.5 is an enlarged view partially illustrating the gas detecting device of FIG.2.

The gas detecting device illustrated in FIGS. 2 and 3 is used together with a circuit shown in FIG. 4, whereby a gas detecting system is constructed. Referring to FIG. 4, a heater power source V1 (a variable DC battery for the illustrated example) is connected across the heater lead 2c through the bonding pads 2a and 2b. A detection power source V2 (a constant DC battery for the illustrated example) is connected to the pair of the detection leads 4e and 4f through the bonding pads 4a and 4b of the detection leads 4e and 4f. A voltmeter Vdet is connected across the bonding pads 4a and 4b. The voltmeter Vdet is electrically coupled to the gas sensitive layer 5 through the contact holes 4c and 4d. during gas detecting operation, the heater lead 2c is heated by the heater power source V1, whereby the pair of detection leads 3e and 3f and the gas sensitive layer 5 are heated. On the other hand, a constant current passes through the gas sensitive layer 5 from the detection power source V2. Thereby, a detection voltage depending on the presence of gas is generated across the contact holes 4c and 4d, and is extracted through the bonding pads 4a and 4b. The extracted detection voltage is indicated by the voltmeter Vdet.

It is noted that the extraction of detection voltage is based on a so-called 4-terminal measurement. Therefore, it is possible to definitely detect only a voltage change truly depending on the presence of gas. In other words, the detection voltage exhibits no change even if there is a variation in contact resistance formed between the gas sensitive layer 5 and the detection leads 3e, 3f. Of course, it is possible to connect the detection power source V2 to the pair of detection leads 4e and 4f and connect the voltmeter Vdet to the pair of detection leads 3e and 3f.

Figure 6:
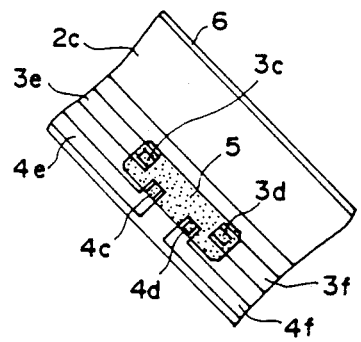
FIG.6 is an enlarged view partially illustrating a variation of the gas detecting device of FIG.2.

The arrangement of the detection leads 3e, 3f, 4e and 4f and contact holes 3c, 3d, 4c and 4d is not limited to the arrangement shown in FIG.2. In the alternative, an arrangement illustrated in FIG.6 may be employed. An end of each of the detection leads 4e and 4f has an L-shaped portion. It is important that the two pairs of detection leads 3e, 3f, and 4e, 4f make contact with the gas sensitive layer 5 without destroying a uniform distribution of temperature around the gas sensitive layer 5.

Therefore, an arbitrary arrangement of the gas detection leads 3e, 3f, 4e and 4f can be employed under the condition where the temperature distribution around the gas sensitive layer 5 is kept uniform.

Figure 7A:
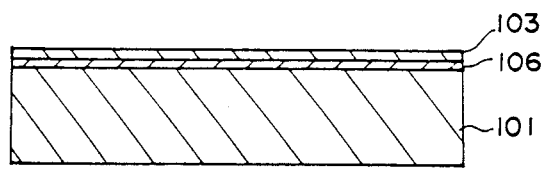
FIGS.7A through 7F are sectional views illustrating different steps of manufacturing the gas detecting device shown in FIGS.2 and 3.
Figure 7B:
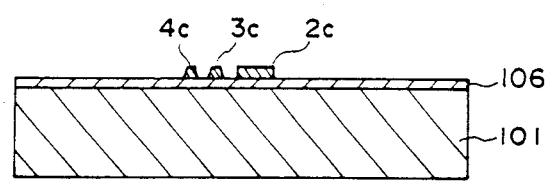
Figure 7C:
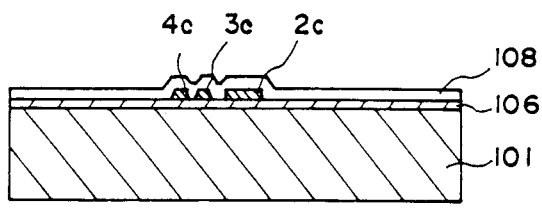
Figure 7D:
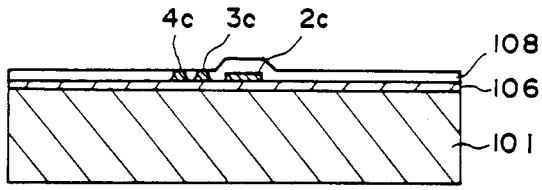
Figure 7E:
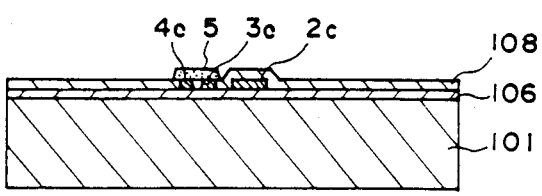
Figure 7F:
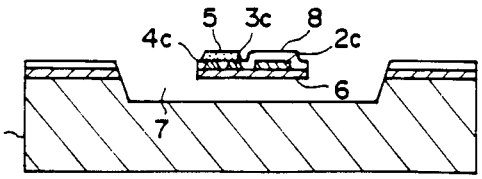

A description is given of a method of manufacturing the gas detecting device illustrated in FIGS.2 and 3 with reference to FIGS.7A through 7F, which are sectional views taken along the line 3—3 shown in FIG.2 observed at different manufacturing steps. Referring to FIG.7A, a silicon dioxide layer 106 is deposited to a thickness of 0.2 to 2 $\mu$m on a silicon substrate 101 by a chemical vapor deposition process, for example. Next, as shown in FIG.7A, a conductive layer 103 of platinum, for example, is formed on the silicon dioxide layer 106 by evaporation, sputtering, chemical vapor deposition or the like, and is then patterned by etching such as argon sputter etching, after depositing a photoresist film. Thereby, the detection leads 3e, 3f, 4e and 4f, and the heater leads 2c are formed. The conductive layer 103 is 0.2 to 2 $\mu$m thick, for example. Then, as shown in FIG.7C, an insulating film 108 formed of a silicon dioxide, for example, is deposited on the entire surface of the substrate 101. Thereafter, as shown in FIG.7D, the insulating film 108 is partially removed so that the contact holes 3c, 3d, 3c, 4d, and holes for forming the bonding pads 2a, 2b, 3a, 3b, 4a, 4b are formed therein. Thereafter, a tin dioxide film is deposited on the entire surface of the substrate 101, and is then patterned by using a rare nitric acid liquid so as to form the gas sensitive layer 5 which makes contact with the detection leads 3e, 3f, 4e and 4f (FIG.7E). Finally, as shown in FIG.7F, the silicon substrate 101, and the insulating layers 106 and 108 are partially etched by using a sodium hydroxide liquid, so that the structure shown in FIGS.2 and 3 is formed.

Figure 8:
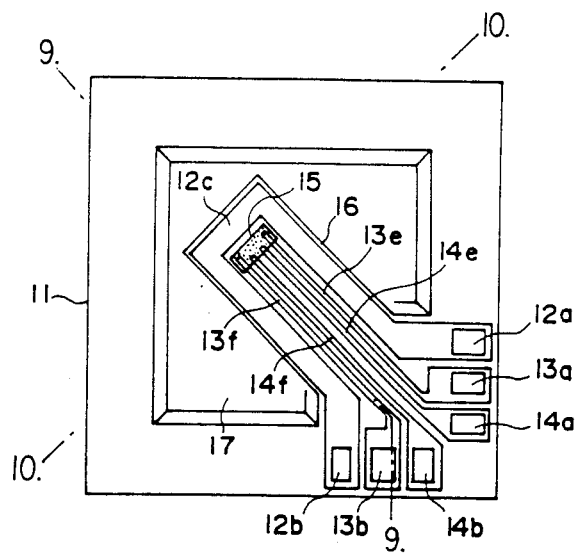
FIG.8 is a plan view of a second embodiment of the present invention.
Figure 9:
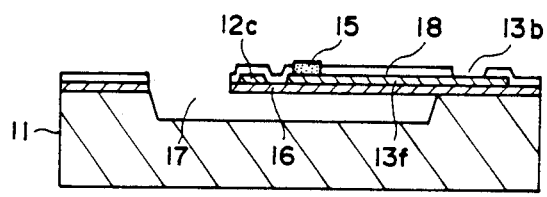
FIG.9 is a sectional view taken along line 9—9 shown in FIG.8.
Figure 10:
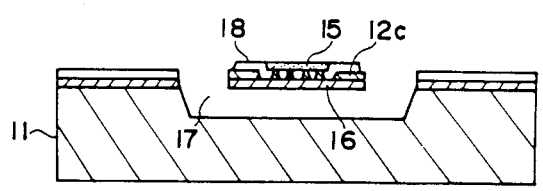
FIG.10 is a sectional view taken along line 10—10 shown in FIG.8.

A description is given of a second embodiment of the present invention with reference to FIGS.8 through 10. The second embodiment is of a cantilever type. A cantilever bridge 16 made of an insulating material diagonally extends over a groove 17 from a corner of a substrate 11. Four detection leads 13e, 13f, 14e and 14f are laid side by side on the cantilever bridge 16 so that the detection leads 14e and 14f are interposed between the detection leads 13e and 13f. The detection lead 14e and 14f are interposed between the detection leads 13e and 13f. A heater lead 12c is arranged so as to surround the arrangement of the detection leads 13e, 13f, 14e and 14f. A passivation layer 18 covers the detection leads 13e, 13f, 14e and 14f, and the heater leads 12c except for contact holes to be formed at end portions of the detection leads 13e, 13f, 14e and 14f, as well as bonding pads 13a, 14b, 14a and 14b to be formed in the detection leads 13e, 13f, 14e and 14f. Surfaces of the end portions of the detection leads 13e, 13f, 14e and 14f are exposed. A gas sensitive layer 15 is formed so as to make contact with the exposed end portions of the detection leads 13e, 13f, 14e and 14f. Each element of the second embodiment may be made of the same as that for the first embodiment.

Figure 11:
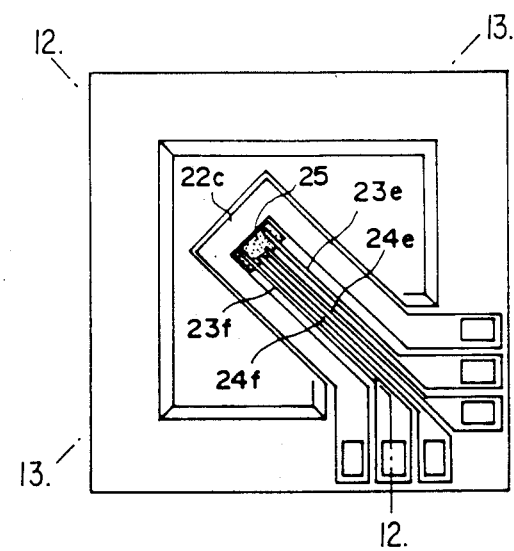
FIG.11 is a plan view of a third embodiment of the present invention.
Figure 12:
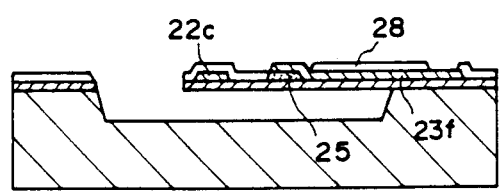
FIG.12 is a sectional view taken along line 12—12 shown in FIG.11.
Figure 13:
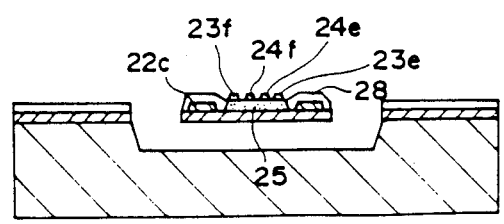
FIG.13 is a sectional view taken along line 13—13 shown in FIG.11.

A description is given of a third embodiment of the present invention with reference to FIGS.11 through 13. The third embodiment corresponds to a variation of the second embodiment. An essential feature of the third embodiment is that a gas sensitive layer 25 is directly formed on a cantilever bridge 26 made of an insulating material, and that end portions of four detection leads 24e, 24f, 25e and 25f formed on the cantilever bridge 26 are laid on the gas sensitive layer 25. As in the case of the second embodiment, the detection leads 24e and 24f are arranged so as to be interposed between the detection leads 23e and 23f. A heater lead 22c is arranged so as to surround the arrangement of the detection leads 23e, 23f, 24e and 24f. In addition to the advantages of the second embodiment, the third embodiment has an advantage that it is difficult for the gas sensitive layer 25 to come off the device.

Figure 14:
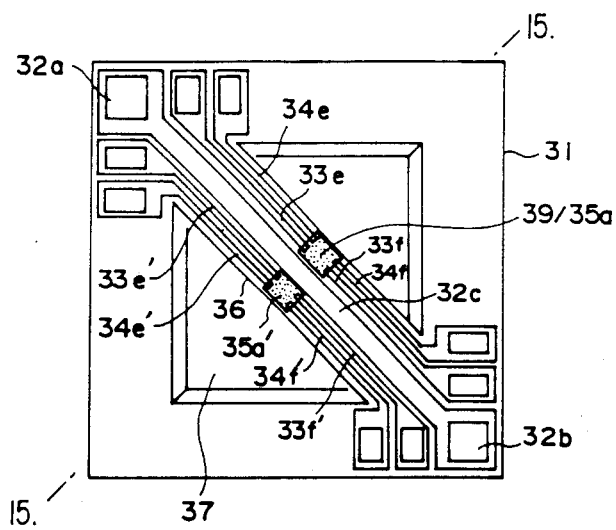
FIG.14 is a plan view of a fourth embodiment of the present invention.
Figure 15:
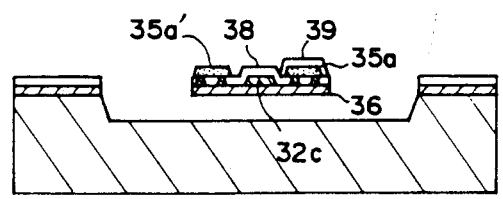
FIG.15 is a sectional view taken along line 15—15 shown in FIG.14.

A fourth embodiment of the present invention is described with reference to FIGS.14 and 15. An essential feature of the fourth embodiment is that a gas sensitive layer 35a' and a temperature sensitive layer 35a are formed on a bridge 36 made of an insulating material which extends over a groove 37 formed in a substrate 31. It is noted that the gas sensitive layer 35a' is used for actually detecting gas, and the temperature sensitive layer 35a is used for compensating the heater driving current to set the heater lead 32c to a desired temperature. It is noted that some gas sensitive materials such as $SnO_2$, $Fe_2O_3$, and ZnO, are also sensitive to heat. The variation in temperature is extracted as a voltage change, and is supplied to a temperature compensating circuit (not shown) including a temperature detecting circuit, which may be identical to that shown in FIG.4. Then the temperature compensating circuit adjusts the heater driving current in accordance with the detected temperature variation.

Figure 16:
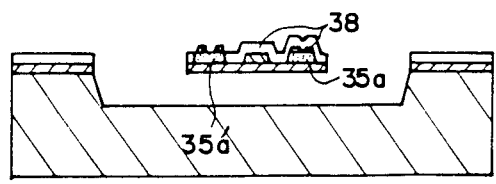
FIG.16 is a sectional view illustrating a variation of the fourth embodiment.

The gas sensitive layer 35a' and the related structure are almost the same as those for the first embodiment of FIGS.2 and 3. That is, four detection leads 33e, 33f, 34e and 34f related to the temperature sensitive layer 35a are formed on the bridge 36. Similarly, four detection leads 33e', 33f', 34e', and 34f' related to the gas sensitive layer 35a' are formed on the bridge 36 so as to run parallel with the arrangement of the detection leads 33e, 33f, 34e and 34f. It is noted that the gas sensitive layer 35a' is exposed for coming in contact with gas, and on the other hand, as shown in FIGS.15 and 16, the temperature sensitive layer 35a is entirely covered by a passivation layer 38 so as to prevent it from being exposed to gas. A heater lead 32 having bonding pads 32a and 32b is formed on the bridge 36 so as to be interposed between a first group consisting of the detection leads 33e', 33f', 34e', and 34f' and a second group consisting of the detection leads 33e, 33f, 34e and 34f. In the alternative, as shown in FIG.16, it is possible to arrange the first and second groups of detection leads so as to be partially overlaid on the gas sensitive layer 35a' and the temperature sensitive layer 35a, respectively, in a way similar to the arrangement shown in FIGS.11 through 13.

Figure 17:
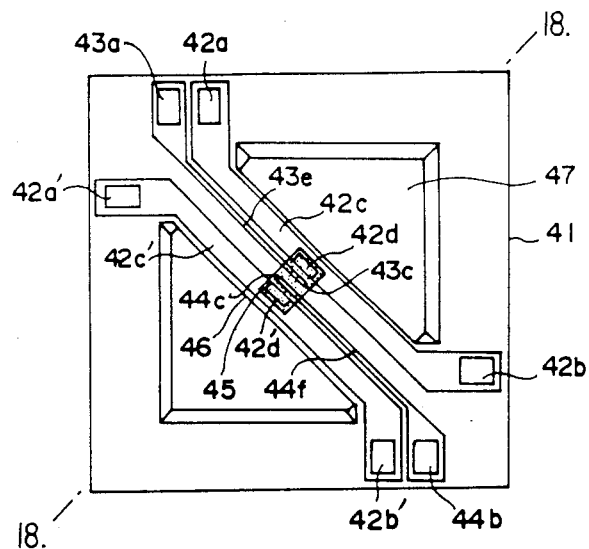
FIG.17 is a plan view of a fifth embodiment of the present invention.
Figure 18:
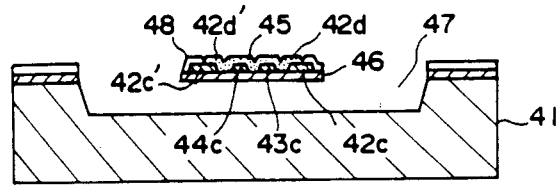
FIG.18 is a sectional view taken along line 18—18 shown in FIG.17.

A fifth embodiment of the present invention is illustrated in FIGS.17 and 18. An essential feature of the fifth embodiment is that two detection leads out of four detection leads to be connected to a gas sensitive layer are also used as heater leads. A pair of heater leads 42c and 42c' is arranged on a bridge 46 made of an insulating material over a groove 47 formed in a substrate 41. A detection lead 43e is arranged on the bridge 46 so as to extend from a gas sensitive layer 45 along the heater lead 42c. A detection lead 44f is arranged on the bridge 46 so as to extend from the gas sensitive layer along the heater lead 42c'. The heater leads 42c and 42c' are wider than the detection leads 43 and 44f. A passivation layer 48 is formed so as to cover the heater leads 42c, 42c', and the detection leads 43e, 44f except for a portion where the gas sensitive layer 45 is to be formed, and portions where bonding pads 42a, 42b, 42a', 42b', 43a, and 44b are to be formed. The gas sensitive layer 45 is formed so as to cover the exposed portions of the heater leads 42c, 42c' and the detection leads 43e, 44f.

Figure 19:
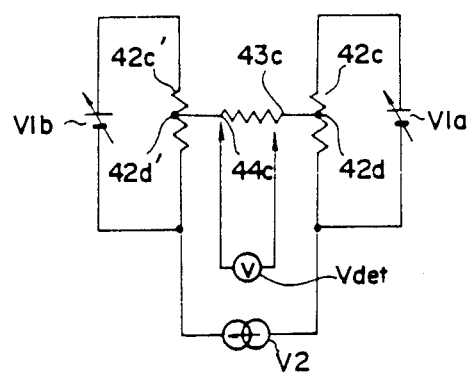
FIG.19 is a circuit diagram of a gas detecting system which uses the gas detecting device shown in FIGS.17 and 18.

Referring to FIG.19, there is illustrated a gas detecting system using the fifth embodiment depicted in FIGS.17 and 18. Referring to FIG.19, a heater power source V1a is connected across the bonding pads 42a and 42b of the heater lead 42c. Similarly, a heater power source V1b is connected across the bonding pads 42a' and 42b' of the heater lead 42c'. A detection power source V2 is connected to one of the two bonding pads of each of the heater leads 42c and 42c, such as the bonding pads 42b and 42b'. A voltmeter Vdet is connected to the bonding pads 43a and 44b. During the gas detecting operation, a constant current is supplied to each of the heater leads 42c and 42c'. It can be seen from FIG.19 that a 4-terminal bridge circuit is formed and therefore a detection voltage obtained at the voltmeter Vdet is not affected by contact resistances formed between the gas sensitive layer 45 and the detection leads 43e, 44f and the heater leads 42c and 42c'. It is to be noted that an area to be heated is smaller than that for each of the first to fourth embodiments, and therefore, power consumption is smaller than that for each of the first to fourth embodiments. Therefore, an elongated life time of the heater leads 42c and 42c' can be obtained. However, in the structure of FIG.19, it is required to use two heater power sources V1a and V1b in order to separate the detection voltage from the heater driving currents passing through the heater leads 42c and 42c'.

Figure 20:
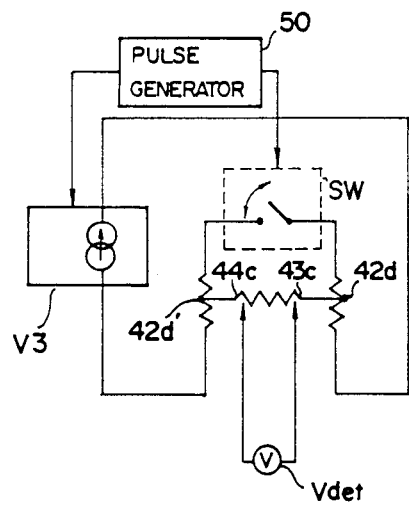
FIG.20 is a circuit diagram of a gas detecting system which uses the gas detecting device shown in FIGS.17 and 18.
Figure 21:
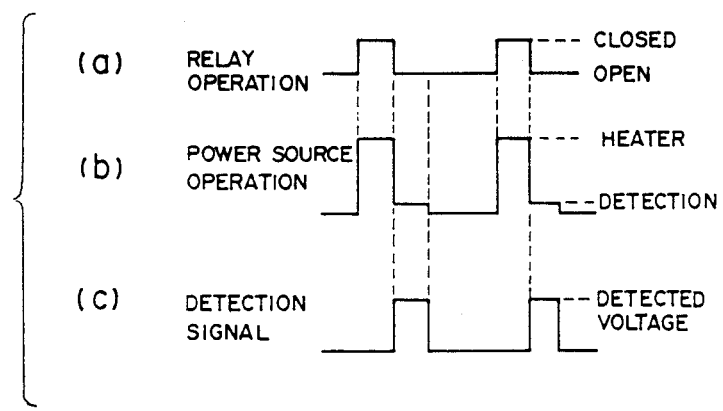
FIG.21 is a waveform diagram of signals observed in the circuit of FIG.20.

A description is given of a modification of the fifth embodiment with reference to FIGS.20 and 21. The modification has an essential feature that a single heater power source is used for driving the gas detecting device of FIGS.17 and 18. Referring to FIG.20, a heater power source V3 is connected to one of the bonding pads related to each of the heater leads 42c and 42c'. The heater power source V3 operates as shown in FIG.21(b). A switch circuit SW is connected to the other bonding pads related to the heater leads 42c and 42c'. The switch circuit SW is controlled by a pulse generator 50 in such a way that it is alternately turned ON and OFF, as shown in FIG.21(a).

In operation, a heater driving current of 20 mA, for example, is supplied to the heater leads 42c and 42c'. For example, temperature of each of the heater leads 42c and 42c' rises up to approximately 350° C. or more after 5 msec from the start of heating. In order to facilitate the gas absorption, the heater driving current is continuously supplied to the heater leads 42c and 42c' for 20 msec. Immediately after the 20 msec application, the heater driving current is set equal to approximately 20 μA. At the same time, the switch circuit SW is turned OFF (open). Thereby, current sequentially passes through the contacts, that is, the contact 42d between the heater lead 42c and the gas sensitive layer 45, the contact 43c between the detection lead 43e and the gas sensitive layer 45, the contact 44c between the detection lead 44f and the gas sensitive layer 45, and the contact 42d' between the heater lead 42c' and the gas sensitive layer 45. Immediately after the current decreases, the heater leads 42c and 42c' are maintained at high temperatures, and therefore, a detection signal shown in FIG.21(c) is indicated by the voltmeter Vout. It is noted that the above-mentioned parameter values are based on the case where the bridge 46 is approximately 2 to 3 μm thick, 60 μm wide, and 200 to 300 μm long, and the heater resistance of the switch circuit SW obtained in the closed state is 50-120 ohms at room temperatures. With the structure shown in FIGS.20 and 21, it becomes possible to use high-resistance heater leads, which makes it possible to reduce the, heater driving current and the thermal capacity of the power source.

Figure 22:
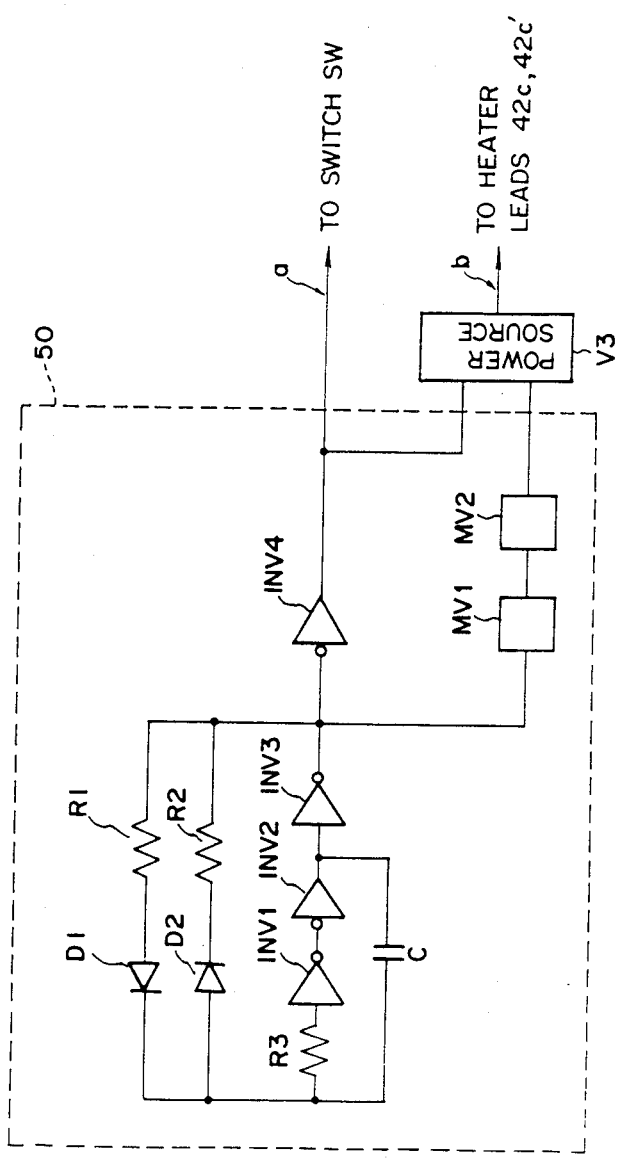
FIG.22 is a circuit diagram of an example of the structure for the pulse generator 50 illustrated in FIG.20.

FIG.22 is a circuit diagram of an example of the structure of the pulse generator 50 shown in FIG.20. The pulse generator 50 includes diodes D1, D2, resistors R1, R2, R3, a capacitor C, inverters INV1-INV4, and monostable multivibrators MV1 and MV2. The anode of the diode is connected to the resistor R1, and the cathode thereof is connected to the anode of the diode D2, the register R3 and the capacitor C. The cathode of the diode D2 is connected to the resistor R2, which is connected to the resistor R1, the inverters INV3 and INV4, and the monostable multivibrator MV1. The inverters INV1 through INV4 are connected in series in this order. The capacitor is connected to the resistor R3 and the output terminal of the inverter INV2. The pulse signal shown in FIG.21(a) is output from the inverter INV4. The pulse signal is also supplied to the heater power source V3. The monostable multivibrator MV2 is connected to the monostable multivibrator MV1. The output signal of the monostable multivibrator MV2 is supplied to the heater power source V3. The heater power source V3 operates as shown in FIG.21(b).

The present invention is not limited to the aforementioned embodiments, and variations and modification may be made without departing from the scope of the present invention.

What is claimed is:

1. A gas detecting device comprising:
   a substrate;
   an insulating layer supported by said substrate;
   first and second pairs of detection leads formed on said insulating layer;
   a heater lead formed on said insulating layer, said first and second pairs of detection leads being heated by passing a heater driving current through said heater lead;
   a gas sensitive layer formed of a gas sensitive material and provided so as to partially make contact with said first and second pairs of detection leads; and
   a passivation layer formed so as to cover said first and second pairs of detection leads and said heater lead, a gas detection signal being output from said gas sensitive layer through one of said first and second pairs of detection leads.

2. A gas detecting device as claimed in claim 1, wherein said detection leads of each of said first and second pairs are aligned in the opposite directions so that opposed ends of detection leads of each of said first and second pairs are spaced from each other.

3. A gas detecting device as claimed in claim 2, wherein said passivation layer has contact holes located at said opposed ends of said detection leads of each of said first and second pairs of detection leads.

4. A gas detecting device as claimed in claim 2, wherein said opposed ends of one of said first and second pairs of detection leads have L-shaped portions, which make contact with said gas sensitive layer.

5. A gas detecting device as claimed in claim 1, said first and second pairs of detection leads run parallel with said heater lead.

6. A gas detecting device as claimed in claim 1, wherein said substrate includes a groove formed in a surface thereof, and said insulating layer is in the shape of a bridge, which extends over said groove.

7. A gas detecting device as claimed in claim 6, wherein said substrate is in the shape of a rectangular chip, and said groove is formed in a center portion of said substrate, and wherein said insulating layer in the shape of a bridge diagonally extends over said groove and connects two corner portions of said substrate.

8. A gas detecting device as claimed in claim 1, wherein said substrate includes a groove formed in a surface thereof, and said insulating layer is in the shape of a cantilever, which extends over said groove from a corner of said substrate.

9. A gas detecting device as claimed in claim 1, wherein said first and second pairs of detection leads extend in the same direction and are arranged side by side, and said detection lead is arranged so as to surround said first and second pairs of detection leads.

10. A gas detecting device as claimed in claim 9, wherein said second pair of detection leads are interposed between said detection leads of said first pair.

11. A gas detecting device as claimed in claim 1, wherein one of said first and second pairs of detection leads is to be supplied with a predetermined voltage, and the other pair is to be connected to a voltmeter.

12. A gas detecting device as claimed in claim 1, wherein said passivation layer has contact holes so as to expose ends of said first and second pairs of detection leads, and wherein said gas sensitive layer is formed on said passivation layer and makes contact with said first and second pairs of detection leads through said contact holes formed in said passivation layer.

13. A gas detecting device as claimed in claim 1, wherein said gas sensitive layer is formed on said insulating layer, and ends of said first and second detection leads are laid on said gas sensitive layer to thereby make contact with the said gas sensitive layer.

14. A gas detecting device comprising:
   a substrate;
   an insulating layer supported by said substrate;
   first, second, third and fourth pairs of detection leads formed on said insulating layer, said detection leads of each of said first, second, third and fourth pairs extending in the opposite directions;
   a heater lead formed on said insulating layer and located between a first group consisting of said first and second pairs of detection leads and a second group consisting of said third and second detection leads, said first to fourth pairs of detection leads being heated by passing a heater driving current through said heater lead;
   a gas sensitive layer formed of a gas sensitive material and provided so as to partially make contact with said first groups of detection leads;
   a temperature sensitive layer formed of a temperature sensitive material and provided so as to partially make contact with said second group of detection leads; and
   a passivation layer formed so as to cover said first and second pairs of detection leads and said heater lead, and said temperature sensitive layer,
   a gas detection signal being output from said gas sensitive layer through one of said first and second pairs of detection leads.

15. A gas detecting device as claimed in claim 14, wherein said passivation layer includes first and second contact holes, and said gas sensitive layer is formed on said passivation layer and makes contact with said first group of detection leads through said first through holes, and wherein said temperature sensitive layer is formed on said passivation layer and makes contact with said second group of detection leads through said second through holes.

16. A gas detecting device as claimed in claim 14, wherein said gas sensitive layer and said temperature sensitive layer are formed on said insulating layer, and wherein end portions of said detection leads of said first group are laid on said gas sensitive layer, and end portions of said detection leads of said second group are laid on said temperature sensitive layer.

17. A gas detecting device as claimed in claim 14, wherein said substrate includes a groove formed in a center portion thereof, and said insulating layer is in the shape of a bridge, which extends over said groove formed in said substrate.

18. A gas detecting apparatus as claimed in claim 14, wherein said gas sensitive layer is formed of a material identical to that of said temperature sensitive material.

19. A gas detecting apparatus as claimed in claim 14, wherein one of said first and second pairs of detection leads is to be supplied with a predetermined voltage, and the other is to be connected to a voltmeter indicating the detected gas.

20. A gas detecting device as claimed in claim 14, wherein one of said third and fourth pairs of detection leads is to be supplied with a predetermined voltage, and the other is to be connected to a voltmeter indicating a temperature of said temperature sensitive layer.

21. A gas detecting device comprising:
a substrate;
an insulating layer supported by said substrate;
a pair of detection leads formed on said insulating layer;
a pair of heater leads formed on said insulating layer, said pair of detection leads being heated by passing a heater driving current through each of said paired heater leads;
a gas sensitive layer formed of a gas sensitive material and provided so as to partially make contact with said pair of detection leads and said pair of heater leads; and
a passivation layer formed so as to cover said pair of detection leads and said pair of heater leads and cover around the said gas sensitive layer,
a gas detection signal being output from said gas sensitive layer through said pair of detection leads.

22. A gas detecting device as claimed in claim 21, wherein said substrate has a groove formed at a center portion thereof, and said insulating layer is in the shape of a bridge, which extends over said groove, and wherein said heater leads of the pair are arranged along opposed edges of said insulating layer, and said detection leads of said pair are interposed between said heater leads and extend in the opposed directions.

23. A gas detecting device as claimed in claim 21, wherein said gas sensitive layer makes contact with end portions of said pair of detection leads and intermediate portions of said pair of heater leads.

24. A gas detecting device as claimed in claim 21, wherein said pair of heater leads is wider than said pair of detection leads.

25. A gas detecting system comprising:
a substrate;
an insulating layer supported by said substrate;
first and second pairs of detection leads formed on said insulating layer;
a heater lead formed on said insulating layer, heating said first and second pairs of detection leads;
a passivation layer formed so as to cover said first and second pairs of detection leads and said heater lead;
a gas sensitive layer formed of a gas sensitive material and provided so as to partially make contact with said first and second pairs of detection leads;
first power source means, connected to said heater lead, for passing a heater driving current through said heater lead;
second power source means, connected to said first pair of detection leads, for applying a predetermined voltage to said gas sensitive layer through said first pair of detection leads; and
voltage monitoring means, connected to said second pair of detection leads, for monitoring a variation in voltage generated in said gas sensitive layer through said second pair of detection leads.

26. A gas detecting system as claimed in claim 25, wherein said first power source means comprises a variable direct current power source.

27. A gas detecting system as claimed in claim 25, wherein said second power source means applies a constant direct current voltage to said second pair of detection leads.

28. A gas detecting system comprising:
a substrate;
an insulating layer supported by said substrate;
a pair of detection leads formed on said insulating layer;
a pair of heater leads formed on said insulating layer, heating said pair of detection leads;
a gas sensitive layer formed of a gas sensitive material and provided so as to partially make contact with said pair of detection leads and said pair of heater leads;
a passivation layer formed so as to cover said pair of detection leads and said pair of heater leads and cover around the said gas sensitive layer;
first power source means, connected to one of said pair of heater leads, for passing a first heater driving current through said one of paired heater leads;
second power source means, connected to the other one of paired heater leads, for passing a second heater driving current through said other one of paired heater leads;
third power source means, connected to said pair of detection leads, for applying a predetermined voltage to said gas sensitive layer through said pair of detection leads; and
voltage monitoring means, connected to said pair of heater leads, for monitoring a variation in voltage generated in said gas sensitive layer through said pair of detection leads.

29. A gas detecting system as claimed in claim 28, wherein each of said first and second power source means comprises a variable direct current power source.

30. A gas detecting system as claimed in claim 28, wherein said third power source means applies a constant direct current voltage to said gas sensitive layer through said paired heater leads.

31. A gas detecting system comprising;
a substrate;
an insulating layer supported by said substrate;
a pair of detection leads formed on said insulating layer;

a pair of heater leads formed on said insulating layer, heating said pair of detection leads;

a gas sensitive layer formed of a gas sensitive material and provided so as to make contact with said pair of detection leads and said pair of heater leads;

a passivation layer formed so as to cover said pair of detection leads and said pair of heater leads and cover around the said gas sensitive layer;

power source means, connected between said heater leads, for periodically supplying said pair of heater leads with a heater driving current;

switching means, connected to said pair of heater leads so as to form a driving current loop consisting of said pair of heater leads and said power source means, for alternately making and breaking said driving current loop; and voltage monitoring means, connected to said pair of gas sensitive layer, for monitoring a variation in voltage generated in said gas sensitive layer.

32. A gas detecting system as claimed in claim 31, further comprising control means for controlling said power source means to periodically supplying said pair of heater leads with said heater driving current and for controlling said switching means to alternately making and breaking said driving current loop.

33. A gas detecting system as claimed in claim 31, wherein said power source means supplies said pair of heater leads with said driving current having a first magnitude when said switching means breaks said driving current loop, and then supplies said pair of heater leads with said driving current having a second magnitude smaller than said first magnitude when said switching means makes said driving current loop.

34. A gas detecting system as claimed in claim 33, said voltage monitoring means output said variation in voltage generated in said gas sensitive layer when said switching means makes said driving current loop.

* * * * *